United States Patent [19]

Barmby

[11] 3,987,080

[45] Oct. 19, 1976

[54] REGENERATION OF VANADIUM-BRONZE AMMOXIDATION CATALYST

[75] Inventor: David S. Barmby, Media, Pa.

[73] Assignee: Sun Ventures, Inc., St. Davids, Pa.

[22] Filed: May 12, 1975

[21] Appl. No.: 576,821

[52] U.S. Cl. .......................... 260/465 C; 252/416; 252/464; 252/476
[51] Int. Cl.² ................. C07C 120/14; B01J 21/20; B01J 23/94
[58] Field of Search ........... 252/416, 476, 464, 461; 260/465 C; 75/134 V; 423/593

[56] References Cited

UNITED STATES PATENTS

| | | | |
|---|---|---|---|
| 2,496,661 | 2/1950 | Denton | 260/465 C |
| 3,367,802 | 2/1968 | Rhodes | 136/120 FC |
| 3,704,251 | 11/1972 | Vrbaski et al. | 260/346.8 |
| 3,803,205 | 4/1974 | Shang et al. | 252/471 |
| 3,845,094 | 10/1974 | Angstadt | 252/461 |
| 3,846,473 | 11/1974 | Shang et al. | 252/476 |

FOREIGN PATENTS OR APPLICATIONS 41-16511   9/1966   Japan .............................. 260/465 C

OTHER PUBLICATIONS

Chemical Abstracts vol. 62 –1965– 9841–g "Catalytic Activity of Vanadium Bronzes" by L. N. Ganyuk et al.

*Primary Examiner*—Winston A. Douglas
*Assistant Examiner*—P. E. Konopka
*Attorney, Agent, or Firm*—J. Edward Hess; Donald R. Johnson; Paul Lipsitz

[57] ABSTRACT

In an ammoxidation system where hydrocarbon, oxygen and ammonia are reacted at a temperature of from about 375°C. to about 450°C. in the presence of a vanadium bronze catalyst, the improvement of regenerating heat damaged catalyst by cooling the catalyst to below about 400°C. and then reheating it to a temperature of from about 510°C. to about 530°C. in the presence of oxygen.

5 Claims, No Drawings

REGENERATION OF VANADIUM-BRONZE AMMOXIDATION CATALYST

It is known to carry out catalyst ammoxidation reactions where a hydrocarbon and ammonia are reacted in the presence or absence of oxygen. Numerous catalysts have been disclosed for such reactions and a particularly useful catalyst particularly for the preparation of aromatic nitriles from lower alkyl substituted aromatic hydrocarbons of the benzene and naphthalene series (e.g., toluene, the xylenes, 2,6-dimethylnaphthalene, etc.) is a vanadium bronze as disclosed in the copending application of Bushick et al., Ser. No. 568,360, filed Apr. 15, 1975.

As disclosed in Ser. No. 568,360 the vanadium bronzes used as ammoxidation catalysts are known materials discussed in numerous prior art disclosures. For example, it is known in the art that the addition of an alkali metal compound to vanadium pentoxide will, when the mixture is heated yield complex materials with anomalous valencies known as a vanadium bronzes. Such lithium bronzes are discussed by Volkov et al., Zh. Neorg. Khim: 17 (6): 1529–1532 (1972). Vanadium bronzes with sodium are described by Pouchard et al., Bull de la Soc. Chimique de France, No. 7, pages 2742–45 (1968), and No. 11 pages 4343–4348 (1967). Similarly, potassium containing vanadium bronzes are discussed by Holtzberg et al., J. Am. Chem, Soc. Vol. 78, pages 1536–40 (1956). Lithium bronzes are described by Hardy et al., Bull de la Soc. Chimique de France, No. 4, 1056–65 (1965) and by Reisman et al Jour. Physical Chemistry 66 1181–85 (1962). Also of interest is the article by P. Hagenmuller entitled "Tungsten Bronzes, Comprehensive Inorganic Chemistry", edited by J. C. Bailar, Jr. et al. and published in 1973 by Pergamon Press.

In the ammoxidation process using the vanadium bronze catalysts, however, it has been found that their catalytic activity may be degraded if they become subject to the high "hot spot" temperatures (i.e., temperatures greater than about 570° C.) which often occurs in the ammoxidation process. This is particularly true when the ammoxidation occurs with oxygen present in the system and it is believed that under such conditions the bronze configuration is destroyed at least in part, being converted to a fully oxidized state. The effectiveness of the catalyst is reduced accordingly and it is toward the solution of this problem that this invention is directed.

In accord with the invention, a heat damaged vanadium bronze catalyst used in ammoxidation reactions is regenerated by cooling the catalyst to a temperature below about 400° C. and then reheating it to a temperature of from about 510° C. to about 530° C. in the presence of oxygen.

The Bronze catalyst materials may be prepared by mixing an appropriate alkali metal compound (e.g., carbonate, oxalate, etc.) with vanadium pentoxide and heating the mixture at an elevated temperature for several hours. Depending upon the amount of alkali metal ion added certain phases will be established in accordance with the particular phase diagram pertinent to the mixture. Thus, for example, the Holtzberg et al. article referred to above describes the potassium bronze system and the sodium system is shown in the article by Slobodin et al. J. Appl. Chem., (USSR) Vol. 38, pp 799–803 (April 1965). Of the above alkali metal vanadium bronzes, all of which may be used in the process of the invention, the preferred bronzes for use as catalyst are the sodium bronzes and mixtures of the various species also may be employed. Preferred species include Bronze I (BZ I) which has an atomic ratio of sodium to vanadium of 0.167, Bronze II (BZ II) where the atomic ratio is 0.417, and an alpha prime phase ($\alpha'$-phase) where the atomic ratio is 0.50. The terms Bronze I and Bronze II are used because these compounds correspond to the compounds called "first BRONZE" and "second BRONZE" by Slobovin and Fotiev, Jour. Applied Chemistry (USSR) 38 Vol. 4 pg. 799 April 1965 where the first bronze is characterized by having 14.3 mole percent of $Na_2O$ in its composition (as does BZ I) and the second bronze has 29.4 mole percent of $Na_2O$ (as does BZ II). These preferred Bronze I and $\alpha'$-phase bronzes may be further characterized by the generic empirical formula $Na_xV_2O_5$ where $x$ is greater than zero and equal to or less than 1. Other bronze systems of the $Na_xV_2O_5$ species are known where x is greater than 1 and these are useful in the process, but are somewhat unstable and therefore not preferred. The BZ I species may be considered as $Na_2O \cdot V_2O_4 \cdot 5V_2O_5$ or $Na_{0.33}V_2O_5$ which is shown together with related members of the series at pages 573 to 575 of the Hagenmuller article as $\beta$-$Na_xV_2O_5$ where x varies from 0.22 to 0.40, the $\beta$ designation indicating the particular crystal phase structure of the compound. The BZ II species may be considered as $5Na_2O \cdot V_2O_4 \cdot 11V_2O_5$ or $Na_{1+x}V_3O_8$ and is shown at page 584 of the Hagenmuller article mentioned above. The $\alpha'$-phase is characterized as $Na_xV_2O_5$ where $x = 0.7$ to 1.0 (see page 577 of the Hagenmuller article). Also characteristic of the bronzes are their x-ray diffraction patterns wherein the strongest lines are as follows:

BZ I: 9.6, 7.3, 4.75, 3.87, 3.47, 3.38, 3.21, 3.11, 3.08, 2.92, 2.90, 2.727, 2.55, 2.45, 2.38, 2.18, 1.97, 1.87, 2.803, 1.74, 1.535, 1.492.

BZ II: 6.9, 7.04, 5.81, 3.87, 3.62, 3.50, 3.45, 3.21, 3.10, 3.01, 3.67, 2.57, 2.43, 2.32, 2.27, 2.02, 1.97, 1.96, 1.81, 1.72, 1.86, 1.504, 1.333, 1.39.

$\alpha'$ phase: 11.3, 5.645, 4.82, 4.436, 3.667, 3.456, 2.967, 2.889, 2.882, 2.799, 2.604, 2.436, 2.412, 2.291, 2.0196, 1.889, 1.803, 1.77, 1.689, 1.635, 1.592, 1.479.

The $\alpha$-prime phase as with the other bronzes may be obtained by the methods described in the literature and placed on the support for use in the process, or it may be made in situ. This is readily achieved by treating the BZ II on the support with a reducing atmosphere (e.g., ammonia) or a stream similar to the hydrocarbon, ammonia and oxygen to hydrocarbon mole ratio of less than about 3.0.

As indicated the catalyst bronzes may comprise a mixture of the above discussed bronzes and preferred catalysts will comprise a mixture predominant in either BZ II or the $\alpha$-prime phase or both. While BZ I used above is operable, it is preferred in order to keep the carbon oxides to a minimum to avoid having a predominant amount of BZ I in the catalyst composition.

The preferred catalyst support used in the ammoxidation process will be comprised of $\alpha$-alumina. $\alpha$-alumina is well known in the art and is exemplified by natural corundum and by the synthetic varieties which are commercially available. These materials have a high density (on the order of about 0.75 to 1.0 gm/cc.) and very low surface area (on the order of $6m^2/gm$ or less). Generally the $\alpha$-alumina will contain enough sodium ions so that the sodium bronzes may be made without any addition of sodium or other alkali metal compounds. But if insufficient sodium is present, enough may be added to give the desired bronze. In making the supported catalyst all that is required is to make an aqueous slurry of powdered (170 mesh or finer) α-alumina, alkali metal salt (preferably carbonate) and $V_2O_5$, evaporate off the water, pelletize and calcine the pellets at about 500°–600° C. for several hours, while passing a slow flow of air through the furnace. Alternatively, and preferably, the catalyst may be placed on the support by an impregnation technique where an aqueous vanadium oxalate solution containing the appropriate amount of alkali metal is deposited onto the α-alumina support, which method is well known in the art.

As pointed out above, in making the catalyst alkali metal ions (usually in the form of the carbonate) are added to ensure that a bronze is formed. In a particularly preferred catalyst system where a sodium-vanadium bronze is desired, the amount of sodium ion employed to make the catalyst will be at a ratio of sodium to vanadium of 0.30 and such catalyst appears to be of high bronze purity devoid of extraneous materials which might degrade catalyst performance.

As indicated, the catalyst support may be comprised of α-alumina but may contain other components such as silica and other metal oxides as well as the normal contaminants found in α-alumina; e.g., iron, magnesium, and the like. However, at least about 75% by weight of the support may be α-alumina.

The amount of catalyst on the support (e.g., catalyst loading) may be from about 1 to 20% by weight, preferably about 3 to 8%. The surface area of the catalysts used in the process is generally quite low being less than $10 m^2/gm$ and usually 1 to $5 m^2/gm$. Pore volume of the catalyst is such that the major proportion of the pores have diameters less than about 1 micron, being on the order of about 0.2 to 1.0 micron.

After a BZ I or a mixed BZ I and BZ II catalyst is prepared, but before its use, it is preferred to age the catalyst by a heat treatment at about 500° C. to about 750° C. for 3 to 4 hours for the purpose of ensuring uniform reaction and distribution of the catalyst on the support. This treatment will also convert most, if not all, of the BZ I to BZ II which is preferred over BZ I.

The ammoxidation reaction with which the catalysts are used is carried out in conventional apparatus, the reaction gases passing over the catalyst in a fixed bed system at reaction temperature and the effluent gases separated into the appropriate product and by-product streams. As stated above the catalysts are particularly useful to make nitriles from alkyl substituted aromatic hydrocarbons of the benzene and naphthalene series. If it is observed during the ammoxidation that the efficiency of the catalyst drops as indicated by fall off in yield or conversion, the regeneration process of the invention is easily carried out in situ. This is accomplished by terminating the ammoxidation reaction and allowing the catalyst bed to drop to a temperature below about 400° C., usually to a temperature of about 375°–400° C. Then, the bed is heated to bring it to a temperature of from about 510° C. to about 530° C., preferably about 520° C. and an oxygen containing stream (usually air) is passed through the bed as the reheating occurs. After the bed is up to about 520° C. the oxygen containing stream is continued through the bed for a short period of time (usually from about 15 to 40 minutes) after which time, the temperature is allowed to drop to the ammoxidation reaction temperature of from about 375° C. to about 500° C. and the hydrocarbon, ammonia and oxygen streams again passed through the regenerated catalyst to continue the ammoxidation.

The following example involving the ammoxidation of p-xylene to terephthalonitrile is illustrative of the process.

EXAMPLE

A fixed bed ammoxidation reactor consisting of a coil of 0.25 inch outside diameter stainless steel tubing packed to a length of 17.5 feet with 8 to 10 mesh size catalyst of a sodium-vanadium bronze which is essentially all BZ II (8% by weight on α-alumina) is used for ammoxidation of p-xylene at 400° C. and 30 psig. The mole ratio of oxygen and ammonia to p-xylene are each 2.5:1 and the contact time is 6 seconds. After ammoxidation proceeded for some time data on the run is obtained and is given in the table below. The ammoxidation reaction was then terminated and the catalyst bed cooled to 400° C. and then air is passed through the bed while the temperature is brought up to 520° C. and held at that temperature for 30 minutes. After cooling the bed back to 400° C. ammoxidation is again started by passing the reactants through the bed at reaction conditions. The data obtained in that run is also shown in the following table:

Table I

|  | Control Catalyst | Regenerated Catalyst |
|---|---|---|
| p-xylene conversion % | 56 | 60 |
| TN*+TPN+ selectivity % | 74 | 82 |
| TPN+(TPN+TN) % | 34 | 48 |
| Plant yield % | 62 | 75 |

*TN = Toluonitrile
+TPN = Terephthalonitrile

In the above table plant yield is calculated on the assumption that the recycled TN gives the same distribution as p-xylene and the formula, based on mole fractions of TN and TPN is as follows:

$$\frac{\%\ Plant}{Yield} = \left[ (TN+TPN)^2 \times \left(\frac{TN}{TN+TPN}\right) + (TN+TPN) \times \left(1 - \frac{TN}{TN+TPN}\right)\right] \times 100$$

As can be seen from the table, the regenerated catalyst is significantly more efficient in giving improved conversion, selectivity, specificity of TPN and plant yield.

The invention claimed is:

1. In an ammoxidation process where hydrocarbon, oxygen and ammonia are reacted at a temperature of from about 375° C. to about 450° C. in the presence of a vanadium bronze catalyst, the improvement of regenerating heat damaged catalyst by cooling the catalyst to below about 400° C. and then reheating it to a temperature of from about 510° C. to about 530° C. in the presence of oxygen.

2. The process of claim 1 where the catalyst is a sodium-vanadium bronze supported on α-alumina.

3. The process of claim 2 where the catalyst is Bronze I.

4. The process of claim 2 where the catalyst is Bronze II.

5. The process of claim 2 where the catalyst is an α-prime phase.

* * * * *